(12) United States Patent
Cho et al.

(10) Patent No.: US 10,401,301 B2
(45) Date of Patent: Sep. 3, 2019

(54) OPTICAL TEST SYSTEM AND METHOD, AND METHOD OF MANUFACTURING SEMICONDUCTOR DEVICE BY USING THE OPTICAL TEST SYSTEM AND METHOD

(71) Applicant: SAMSUNG ELECTRONICS CO., LTD., Suwon-si, Gyeonggi-do (KR)

(72) Inventors: Seongkeun Cho, Suwon-si (KR); Akinori Okubo, Hwaseong-si (KR); Tae Hyun Kim, Suwon-si (KR); Sangwoo Bae, Seoul (KR); Janghwi Lee, Suwon-si (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/940,011

(22) Filed: Mar. 29, 2018

(65) Prior Publication Data

US 2019/0113463 A1 Apr. 18, 2019

(30) Foreign Application Priority Data

Oct. 12, 2017 (KR) .................. 10-2017-0132283

(51) Int. Cl.
*G01N 21/21* (2006.01)
*G01N 21/88* (2006.01)
(Continued)

(52) U.S. Cl.
CPC ......... *G01N 21/8806* (2013.01); *G01N 21/21* (2013.01); *G01N 21/9501* (2013.01);
(Continued)

(58) Field of Classification Search
CPC .............. G01N 21/8806; G01N 21/21; G01N 21/9501; H01L 22/12; H01L 21/67288
(Continued)

(56) References Cited

U.S. PATENT DOCUMENTS 7,006,224 B2 2/2006 Some
7,075,650 B1 * 7/2006 Johs .................... G01N 21/211
356/369

(Continued)

FOREIGN PATENT DOCUMENTS

JP          4663529 B2    4/2011
KR  10-2016-0116576 A    10/2016

OTHER PUBLICATIONS

Van der Walle et al., "Implementation of background scattering variance reduction on the Rapid Nano particle scanner", Proceedings of SPIE, vol. 9050, 2014.

*Primary Examiner* — Roy M Punnoose
(74) *Attorney, Agent, or Firm* — Lee & Morse, P.C.

(57) ABSTRACT

An optical test system includes a stage region to accommodate an object to be tested, a first incident optical system which changes a first polarization state of a first light beam to a second polarization state and provide the first light beam in the second polarization state to the stage region in a first direction at a first incident angle which is not a right angle, a second incident optical system which changes a third polarization state of a second light beam to a fourth polarization state and inputs the second light beam in the fourth polarization state to the stage region in a second direction at a second incident angle which is not a right angle, and a main optical system to detect a first reflected light beam reflected from the stage region at a first reflection angle different from the first and second incident.

20 Claims, 14 Drawing Sheets

(51) Int. Cl.
*G01N 21/95* (2006.01)
*H01L 21/67* (2006.01)
*H01L 21/66* (2006.01)

(52) U.S. Cl.
CPC ........ *H01L 21/67288* (2013.01); *H01L 22/12* (2013.01); *G01N 2021/8848* (2013.01); *G01N 2201/0683* (2013.01)

(58) Field of Classification Search
USPC .......................................................... 356/369
See application file for complete search history.

(56) References Cited

U.S. PATENT DOCUMENTS

| | | | |
|---|---|---|---|
| 7,221,444 B1* | 5/2007 | Zhao | G01N 21/8806 356/237.1 |
| 7,295,305 B2* | 11/2007 | Yoshida | G01N 21/4788 356/237.5 |
| 7,454,052 B2 | 11/2008 | Smilansky et al. | |
| 8,830,465 B2* | 9/2014 | Taniguchi | G01N 21/956 356/369 |
| 9,046,474 B2 | 6/2015 | Kwak et al. | |
| 9,239,295 B2 | 1/2016 | Peng et al. | |
| 9,267,879 B2 | 2/2016 | Ko et al. | |
| 9,612,212 B1 | 4/2017 | Leem et al. | |
| 2005/0062963 A1* | 3/2005 | Yoshida | G01N 21/4788 356/237.5 |
| 2011/0149275 A1* | 6/2011 | Nakano | G01N 21/9501 356/237.2 |
| 2016/0293139 A1 | 10/2016 | Kwon | |
| 2018/0073979 A1 | 3/2018 | Cho et al. | |

* cited by examiner

OPTICAL TEST SYSTEM AND METHOD, AND METHOD OF MANUFACTURING SEMICONDUCTOR DEVICE BY USING THE OPTICAL TEST SYSTEM AND METHOD

CROSS-REFERENCE TO RELATED APPLICATION

Korean Patent Application No. 10-2017-0132283, filed on Oct. 12, 2017, in the Korean Intellectual Property Office, and entitled: "Optical Test System and Method, and Method of Manufacturing Semiconductor Device by Using the Optical Test System and Method," is incorporated by reference herein in its entirety.

BACKGROUND

1. Field

Embodiments relate to an optical test system and method, and a method of manufacturing a semiconductor device by using the optical test system and method.

2. Description of the Related Art

Defects existing in the surface of a semiconductor wafer or a semiconductor device can affect the reliability and yield of the semiconductor wafer or the semiconductor device. For defect detection, various methods using light can be utilized. However, a defect of a certain size or less may be difficult to distinguish from noise due to the roughness of the surface of the semiconductor wafer or the semiconductor device.

SUMMARY

According to some embodiments, there is provided an optical test system including a stage region to accommodate an object to be tested, a first incident optical system to change a first polarization state of a first light beam to a second polarization state and to provide the first light beam in the second polarization state to the stage region in a first direction at a first incident angle which is not a right angle, a second incident optical system to change a third polarization state of a second light beam to a fourth polarization state and to provide the second light beam in the fourth polarization state to the stage region in a second direction, which is different from the first direction by a first angle, at a second incident angle which is not a right angle, and a main optical system to detect a first reflected light beam reflected at a first reflection angle different from the first and second incident angles among a plurality of reflected light beams obtained after the first light beam in the second polarization state is reflected from the stage region.

According to some embodiments, there is provided a method of manufacturing a semiconductor device, the method including providing an object to be tested and performing an optical test on the object to be tested. Performing the optical test on the object to be tested includes changing a first polarization state of a first light beam to a second polarization state, providing the first light beam in the second polarization state to a test region of the object to be tested in a first direction at a first incident angle which is not a right angle, detecting a first reflected light beam reflected at a first reflection angle different from the first incident angle among a plurality of reflected light beams obtained after the first light beam in the second polarization state is incident on the test region and then reflected from the test region, obtaining first image data by using the first reflected light beam, changing a third polarization state of a second light beam to a fourth polarization state, providing the second light beam in the fourth polarization state to the test region in a second direction, which is different from the first direction by a first angle, at a second incident angle which is not a right angle, detecting a second reflected light beam reflected at a second reflection angle different from the second incident angle among the reflected light beams obtained after the second light beam in the fourth polarization state is incident on the test region and then reflected from the test region, obtaining second image data by using the second reflected light beam, and generating final image data by processing the first image data and the second image data.

According to some embodiments, there is provided an optical test method comprising, changing a first polarization state of a first light beam to a second polarization state, providing the first light beam in the second polarization state to a stage region in a first direction at a first incident angle which is not a right angle, detecting a first reflected light beam reflected at a first reflection angle different from the first incident angle among a plurality of reflected light beams obtained after the first light beam in the second polarization state is reflected from the stage region, changing a third polarization state of a second light beam to a fourth polarization state, providing the second light beam in the fourth polarization state to the stage region in a second direction, which is different from the first direction by a first angle, at a second incident angle which is not a right angle, and detecting a second reflected light beam reflected at a second reflection angle different from the second incident angle among the reflected light beams obtained after the second light beam in the fourth polarization state is incident on the stage region and then reflected from the stage region.

BRIEF DESCRIPTION OF THE DRAWINGS

Features will become apparent to those of skill in the art by describing in detail exemplary embodiments with reference to the attached drawings in which.

DETAILED DESCRIPTION

An optical test system according to embodiments will now be described with reference to FIGS. 1 through 8.

Figure 1:
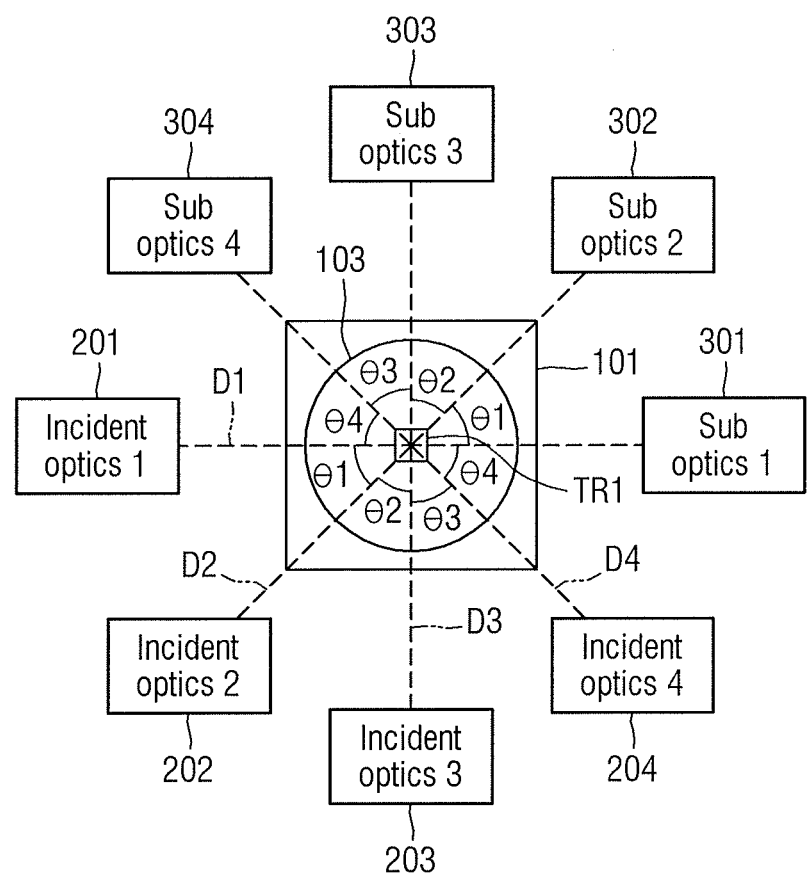
FIG. 1 illustrates a conceptual plan view of an optical test system according to embodiments.
Figure 2:
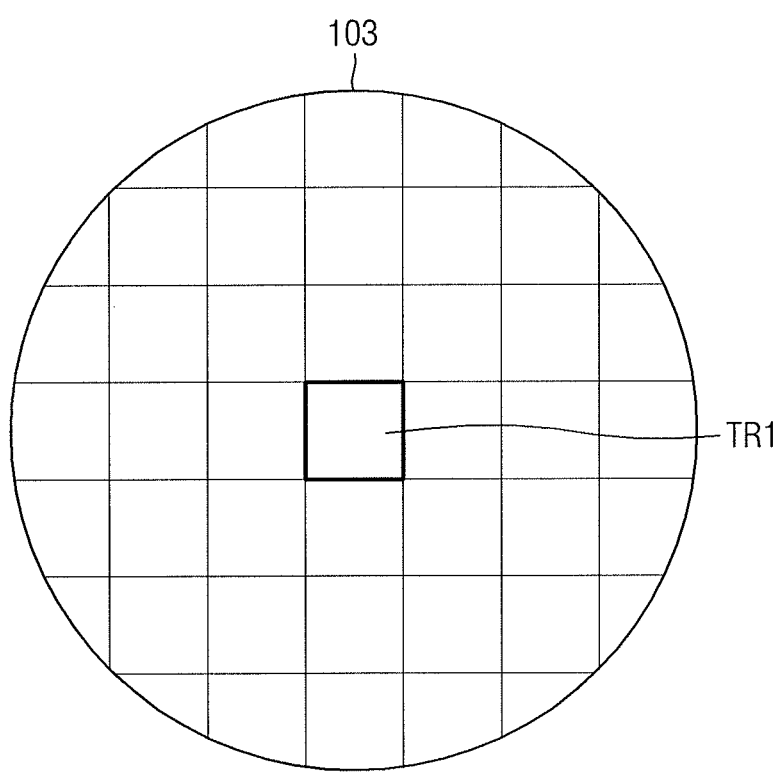
FIG. 2 illustrates an object to be tested and a test region of FIG. 1.
Figure 3:
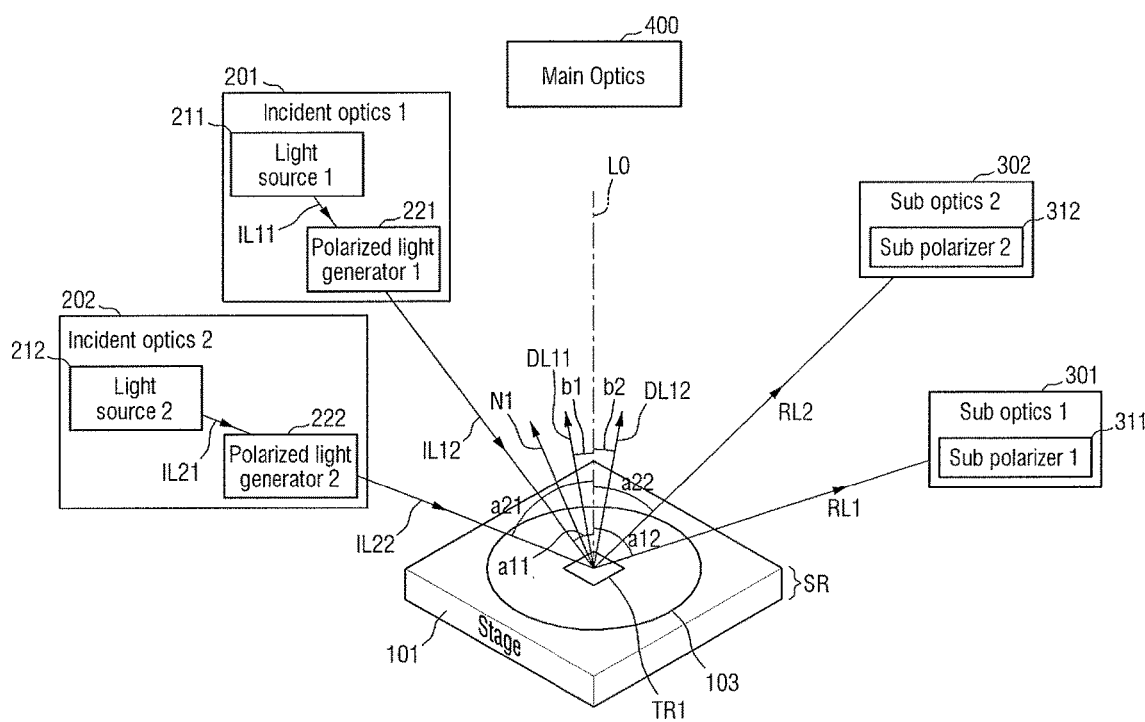
FIG. 3 illustrates a side view of the optical test system of FIG. 1 to describe the optical test system according to the embodiments.
Figure 4:
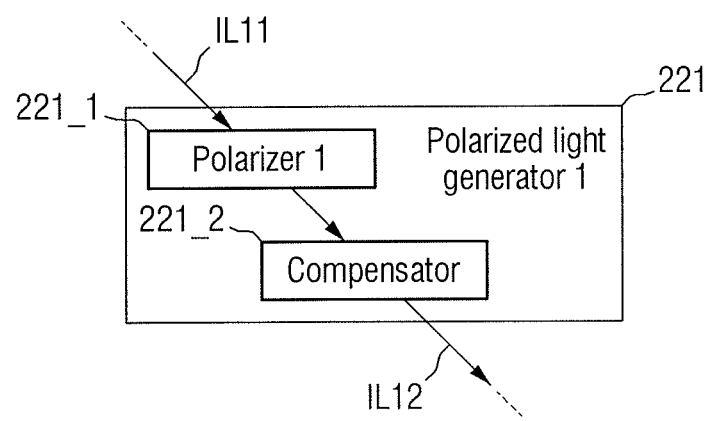
FIG. 4 illustrates a first polarized light generator of FIG. 3.

FIG. 1 is a conceptual plan view of an optical test system according to embodiments. FIG. 2 illustrates an object 103 to be tested and a test region TR1 of FIG. 1. FIG. 3 shows a side view of the optical test system of FIG. 1 to describe the optical test system according to the embodiments. In FIG. 3, a third incident optical system 203, a fourth incident optical system 204, a third sub-optical system 303 and a fourth sub-optical system 304 of FIG. 1 are omitted for clarity of illustration. FIG. 4 illustrates a first polarized light generator 221 of FIG. 3.

Referring to FIGS. 1 through 4, the optical test system according to the embodiments may include first through fourth incident optical systems 201 through 204, first through fourth sub-optical systems 301 through 304, and a stage 101 for receiving the object 103 to be tested.

A stage region SR may include the stage 101 for receiving the object 103 to be tested. The object 103 to be tested may be, for example, a semiconductor wafer or a patterned semiconductor device. A plurality of regions of the object 103 to be tested may include the test region TR1 which is a region to be tested by the optical test system.

The first through fourth incident optical systems 201, 202, 203, and 204 may be disposed in different directions from the stage region SR (specifically, the test region TR1).

For example, the first incident optical system 201 may be disposed in a first direction D1 from the test region TR1. The second incident optical system 202 may be disposed in a second direction D2 which is different from the first direction D1 by a first angle θ1. That is, the second incident optical system 202 may be separated from the first incident optical system 201 by the first angle θ1. The third incident optical system 203 may be disposed in a third direction D3 which is different from the first direction D1 by the sum of the first angle θ1 and a second angle θ2. That is, the third incident optical system 203 may be separated from the second incident optical system 202 by the second angle θ2. The fourth incident optical system 204 may be disposed in a fourth direction D4 which is different from the first direction D1 by the sum of the first angle θ1, the second angle θ2 and a third angle θ3. That is, the fourth incident optical system 204 may be separated from the third incident optical system 203 by the third angle θ3.

The first through fourth sub-optical systems 301, 302, 303. and 304 may be placed to correspond to the first through fourth incident optical systems 201 through 204, respectively.

For example, the first sub-optical system 301 may be placed to face the first incident optical system 201 in the first direction D1. The first sub-optical system 301 may be separated from the fourth incident optical system 204 by a fourth angle θ4. The second sub-optical system 302 may be placed to face the second incident optical system 202 in the second direction D2. The second sub-optical system 302 may be separated from the first sub-optical system 301 by the first angle θ1. The third sub-optical system 303 may be placed to face the third incident optical system 203 in the third direction D3. The third sub-optical system 303 may be separated from the second sub-optical system 302 by the second angle θ2. The fourth sub-optical system 304 may be placed to face the fourth incident optical system 204 in the fourth direction D4. The fourth sub-optical system 304 may be separated from the third sub-optical system 303 by the third angle θ3. In addition, the fourth sub-optical system 304 may be separated from the first incident optical system 201 by the fourth angle θ4.

The first through fourth incident optical systems 201, 202, 203, and 204 may be paired with the first through fourth sub-optical systems 301 through 304, respectively. For example, the first incident optical system 201 may be paired with the first sub-optical system 301. When the first incident optical system 201 and the first sub-optical system 301 are paired with each other, they may face each other in the same plane. The sum of the first through fourth angles θ1 through θ4 may be 180 degrees.

Although four incident optical systems 201, 202, 203, and 204 are illustrated in the drawings, the technical idea of embodiments is not limited to this case. For example, a greater or smaller number of incident optical systems may be provided as needed. If n (n is a natural number) incident optical systems are arranged between the first incident optical system 201 and the first sub-optical system 301, the sum of an angle from the direction in which the first incident optical system 201 is disposed to a direction in which an $n^{th}$ incident optical system is disposed and an angle from the direction in which the $n^{th}$ incident optical system is disposed to the direction in which the first sub-optical system 301 is disposed may be 180 degrees.

In some embodiments, the first through fourth incident optical systems 201, 202, 203, and 204, and the first through fourth sub-optical systems 301, 302, 303, and 304 may simultaneously perform an optical test on the test region TR1. Alternatively, in some embodiments, the first through fourth incident optical systems 201, 202, 203 and 204, and the first through fourth sub-optical systems 301, 302, 303, and 304 may sequentially perform an optical test on the test region TRI.

Alternatively, in some embodiments, the first incident optical system 201 and the first sub-optical system 301 may test the test area TR1 at a position in the first direction D1. Then, the first incident optical system 201 and the first sub-optical system 301 may move to a position where the second incident optical system 202 and the second sub-optical system 302 illustrated in FIG. 1 are disposed and test the test region TR1 at the position in the second direction D2. In this case, the second through fourth incident optical systems 202 through 204 and the second through fourth sub-optical systems 302 through 304 illustrated in FIG. 1 indicate a trajectory along which the first incident optical system 201 and the first sub-optical system 301 move to perform an optical test.

The first incident optical system 201 may include a first light source 211 and a first polarized light generator 221. The first light source 211 may provide a first light beam IL11 in a first polarization state to the first polarized light generator 221. The first polarized light generator 221 may change the first polarization state of the first light beam IL11 to a second polarization state. A first light beam IL12 in the second polarization state may be incident on the stage region SR at a first incident angle a11. The second polarization state may be, e.g., an elliptical polarization state. That is, the first polarized light generator 221 may change the polarization state of incident light to, e.g., the elliptical polarization state.

As shown in FIG. 4, the first polarized light generator 221 may include, e.g., a first polarizer 221_1 and a compensator 221_2. The first polarizer 221_1 and the compensator 221_2 may change the first light beam IL11 in the first polarization state to the first light beam IL12 in the second polarization state.

In some embodiments, each of the first polarizer 221_1 and the compensator 221_2 may be rotated according to a first change condition in order to change the first light beam IL11 in the first polarization state to the first light beam IL12 in the second polarization state. The first change condition and the rotation of each of the first polarizer 221_1 and the compensator 221_2 will be described in detail later.

The first light source 211 and the first polarized light generator 221 may provide the first light beam IL12 in the second polarization state to the test region TR1 at the first incident angle a11. Here, the first incident angle a11 may be a value measured based on a virtual line L0 perpendicular to an upper surface of the stage 101. In other words, the first incident optical system 201 may provide the first light beam IL12 in the second polarization state to the stage region SR in the first direction D1 at the first incident angle a11.

The second incident optical system 202 may include a second light source 212 and a second polarized light generator 222. The second light source 212 may provide a second light beam IL21 in a third polarization state to the second polarized light generator 222. The second polarized light generator 222 may change the third polarization state to a fourth polarization state. A second light beam IL22 in the fourth polarization state may be incident on the stage region SR at a second incident angle a21. The fourth polarization state may be, e.g., an elliptical polarization state. That is, the second polarized light generator 222 may change the polarization state of incident light to, e.g., the elliptical polarization state.

Like the first polarized light generator 221, the second polarized light generator 222 may include, e.g., a second polarizer and a compensator. The second polarizer and the compensator may change the second light beam IL21 in the third polarization state to the second light beam IL22 in the fourth polarization state.

In some embodiments, each of the second polarizer and the compensator may be rotated according to a second change condition in order to change the second light beam IL21 in the third polarization state to the second light beam IL22 in the fourth polarization state. The second change condition and the rotation of each of the second polarizer and the compensator will be described in detail later.

The second light source 212 and the second polarized light generator 222 may provide the second light beam IL22 in the fourth polarization state to the test region TR1 at the second incident angle a21. Here, the second incident angle a21 may be a value measured based on the virtual line L0 perpendicular to the upper surface of the stage 101. In other words, the second incident optical system 202 may provide the second light beam IL22 in the fourth polarization state to the stage region SR in the second direction D2 at the second incident angle a21.

Like the first incident optical system 201 and the second incident optical system 202, each of the third incident optical system 203 and the fourth incident optical system 204 may include a light source and a polarized light generator for changing the polarization state of light generated from the light source. Light beams that pass through the polarized light generators may be incident on the stage region SR at third and fourth incident angles which are not right angles. The polarized light generator of each of the third incident optical system 203 and the fourth incident optical system 204 may also include a polarizer and a compensator. The polarizer and the compensator included in the polarized light generator of each of the third incident optical system 203 and the fourth incident optical system 204 may be rotated at a certain angle to change the polarization state. In some embodiments, the first incident angle a11, the second incident angle a21, the third incident angle, and the fourth incident angle may be the same.

The first incident angle a11 and the second incident angle a21 may not be right angles. Further, the incident angle of a light beam provided to the stage region SR by each of the third incident optical system 203 and the fourth incident optical system 204 may not be right angles. In other words, light beams provided to the stage region SR by the first through fourth incident optical systems 201, 202, 203, and 204 may not be perpendicular to the upper surface of the stage 101, e.g., at an angle relative to the virtual line L0.

Although a case where each of the first through fourth incident optical systems 201, 202, 203, and 204 includes a light source and a polarized light generator has been described above, the technical idea of embodiments is not limited to this case. For example, each of the first through fourth incident optical systems 201, 202, 203, and 204 may include various elements for elliptically polarizing light to be incident on the stage region SR, such as a monochromator or a collimator.

After light (e.g., the first light beam IL12 in the second polarization state and the second light beam IL22 in the fourth polarization state) is incident on the stage region SR, it may be reflected from the stage region SR. For example, a plurality of reflected light beams (e.g., DL11, DL12, RL1, RL2, and N1) may include light beams reflected from the stage region SR after being incident on the stage region SR by the first through fourth incident optical systems 201 through 204.

The first through fourth sub-optical systems 301, 302, 303, and 304 may receive specularly reflected light beams among the reflected light beams (e.g., DL11, DL12, RL1, RL2, and N1) obtained after the light beams incident on the stage region SR by the first through fourth incident optical systems 201, 202, 203 and 204 are reflected from the stage region SR. For example, in FIG. 3, the specularly reflected light beams are RL1 and RL2.

Reflected light beams (e.g., DL11, DL12, and N1) other than the specularly reflected light beams from the reflected light beams (e.g., DL11, DL12, RL1, RL2, and N1), e.g., noise and diffusely reflected light beams, may be received by a main optical system 400, described in detail later. Each of the reflected light beams (e.g., DL11, DL12, and N1) other than the specularly reflected light beams (e.g., RL1 and RL2) may be a light beam reflected from the stage region SR at a reflection angle (e.g., a third reflection angle b1 or a fourth reflection angle b2) different in size from each of the first incident angle a11 and the second incident angle a21. In other words, each of the third reflection angle b1 and the fourth reflection angle b2 may not be the same as, e.g., may be different from, any of the first incident angle a11 and the second incident angle a21. Here, different means having a different absolute value relative to the virtual line L0.

Further, each of the third reflection angle b1 and the fourth reflection angle b2 may not be the same as, e.g., may be different from, the incident angles of light beams incident on the stage region SR by the third and fourth incident optical systems 203 and 204. The main optical system 400 will be described in detail later.

The first sub-optical system 301 may receive a first reflected light beam RL1 obtained after the first light beam IL12 in the second polarized state incident on the stage region SR is specularly reflected. In other words, the first reflected light beam RL1 may be a light beam reflected from the stage region SR at a first reflection angle a12. The first reflection angle a12 may be the same as the first incident angle a11. As used herein, the same is to mean having a same absolute value relative to the virtual line L0. The first reflected light beam RL1 may be, for example, a linearly polarized light beam.

The first sub-optical system 301 may include a first sub-polarizer 311. In some embodiments, the first sub-polarizer 311 may receive the first reflected light beam RL1 and transmit a portion of the amount of the first reflected light beam RL1. For example, the first sub-polarizer 311 may pass about $1/200,000^{th}$ or less of the amount of the first reflected light RL1. Alternatively, in some embodiments, the first sub-polarizer 311 may block, e.g., completely block, the received first reflected light beam RL1. The first sub-polarizer 311 may be rotated according to a first blocking condition in order to transmit a portion of the amount of the first reflected light beam RL1 or block the first reflected light beam RL1.

The first sub-optical system 301 may further include, for example, a detector. The detector may detect light tranmitted from the first sub-polarizer 311 and generate an image of the detected light. In some embodiments, the detector may be a charge coupled device (CCD).

In some embodiments, when the test region TR1 is not defective, the first reflected light beam RL1 may be blocked, e.g., completely blocked, by the first sub-polarizer 311 under the first blocking condition. When the test region TR1 is defective, the first reflected light beam RL1 may include a light component blocked by the first sub-polarizer 311 and a light component DL0 not blocked, e.g., transmitted, by the first sub-polarizer 311 under the first blocking condition. In this case, the detector of the first sub-optical system 301 may detect the light component DL0 not blocked by the first sub-polarizer 311. The light component DL0 not blocked by the first sub-polarizer 311 under the first blocking condition may indicate that a defect exists in the test region TR1.

In some embodiments, when the test region TRI is not defective, only a portion of the amount of the first reflected light beam RL1 may pass through the first sub-polarizer 311 under the first blocking condition. When the test region TRI is defective, the light component DL0 passing through the first sub-polarizer 311 may include the portion of the amount of the first reflected light beam RL1 and another portion of the amount of the first reflected light beam RL1 under the first blocking condition. The another portion of the amount of the first reflected light beam RL1 from the light component DL0 may indicate that a defect exists in the test region TR1.

The first blocking condition and the rotation of the first sub-polarizer 311 will be described in more detail later.

The second sub-optical system 302 may receive a second reflected light beam RL2 obtained after the second light beam IL22 in the fourth polarization state incident on the stage region SR is specularly reflected. In other words, the second reflected light beam RL2 may be a light beam reflected from the stage region SR at a second reflection angle a22. The second reflection angle a22 may be the same as the second incident angle a21. The second reflected light beam RL2 may be, e.g., a linearly polarized light beam.

The second sub-optical system 302 may include a second sub-polarizer 312. The second through fourth sub-optical systems 302 through 304 may perform substantially similar functions to the first sub-optical system 301.

Figure 5:
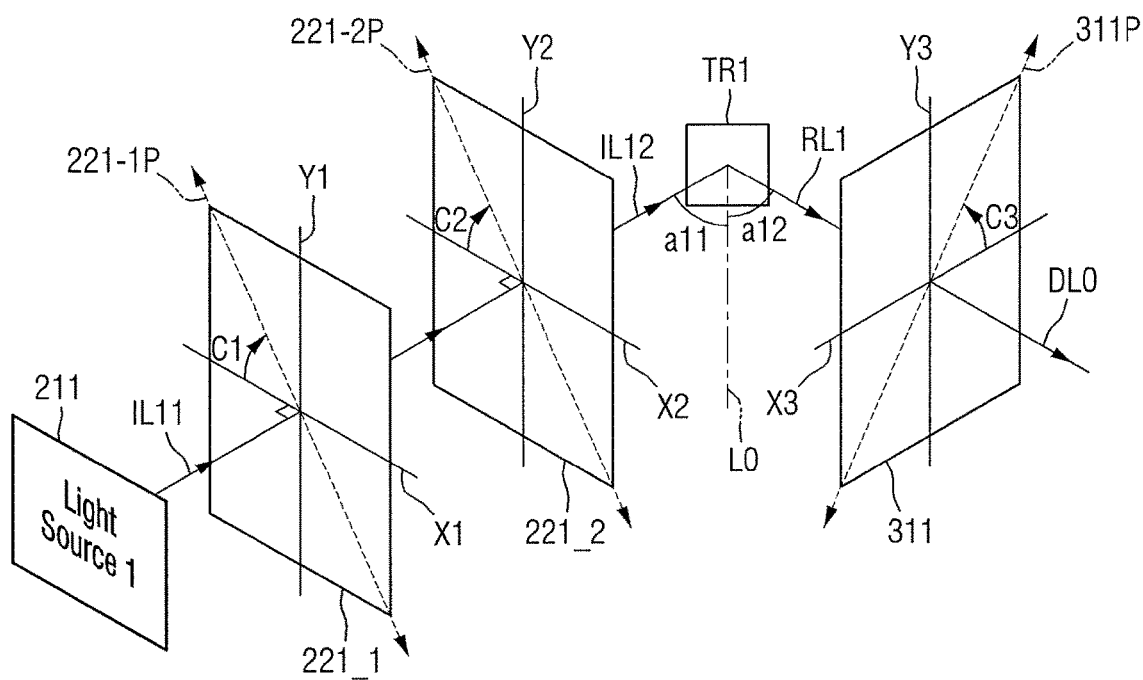
FIG. 5 illustrates a diagram for explaining a first change condition and a first blocking condition of the optical test system of FIG. 1.

FIG. 5 is a diagram for explaining the first change condition and the first blocking condition of the optical test system of FIG. 1. For clarity, any redundant description will be omitted.

The first light beam IL11 in the first polarization state may pass through the first polarizer 221_1 to be incident on the compensator 221_2. The first light beam IL11 passing through the compensator 221_2 may be the first light beam IL12 in the second polarization state. The first polarizer 221_1 and the compensator 221_2 may be rotated at a certain angle according to the first change condition in order to change the first light beam IL11 in the first polarization state to the first light beam IL12 in the second polarization state.

For example, first and second x-axis directions X1 and X2 may be perpendicular to the traveling direction of the first light beam IL11 in the first polarization state. The first and second x-axis directions X1 and X2 may be, e.g., p-polarization directions. First and second y-axis directions Y1 and Y2 may intersect the first and second x-axis directions X1 and X2 and the travelling direction of the first light beam IL11 in the first polarization state and may be perpendicular to the first and second x-axis directions X1 and X2 and the traveling direction of the first light beam IL11 in the first polarization state, respectively. The first and second y-axis directions Y1 and Y2 may be, e.g., s-polarization directions.

A polarization direction 221_1P of the first polarizer 221_1 may be rotated by a first rotation angle C1 with respect to the first x-axis direction X1. A polarization direction 221_2P of the compensator 221_2 may be rotated by a second rotation angle C2 with respect to the second x-axis direction X2. Here, the first rotation angle C1 and the second rotation angle C2 may be included in the first change condition. As the first polarizer 221_1 and the compensator 221_2 are rotated by the first rotation angle C1 and the second rotation angle C2, respectively, the first light beam IL11 in the first polarization state may be changed into the first light beam IL12 in the second polarization state.

The first reflected light beam RL1 obtained after the first light beam IL12 in the second polarization state is incident on the test region TR1 and then reflected from the test region TR1 may be incident on the first sub-polarizer 311. The first sub-polarizer 311 may be rotated at a certain angle according to the first blocking condition in order to block the first reflected light beam RL1 in the linear polarization state or to pass only a portion of the amount of the first reflected light beam RL1.

For example, a third x-axis direction X3 may be perpendicular to the traveling direction of the first reflected light RL1. The third x-axis direction X3 may be, e.g., a p-polarization direction. A third y-axis direction Y3 may intersect the third x-axis direction X3 and the traveling direction of the first reflected light beam RL1 and may be perpendicular to the third x-axis direction X3 and the travelling direction of the first reflected light beam RL1. The third y-axis direction Y3 may be, for example, an s-polarization direction.

A polarization direction 311P of the first sub-polarizer 311 may be rotated by a third rotation angle C3 with respect to the third x-axis direction X3. Here, the third rotation angle C3 may be included in the first blocking condition. As the first sub-polarizer 311 is rotated by the third rotation angle C3, the first reflected light beam RL1 may be blocked by the first sub-polarizer 311 or a portion of the amount of the first reflected light beam RL1 may be passed.

In the drawing, the first polarizer 221_1, the compensator 221_2, and the first sub-polarizer 311 are rotated in a clockwise direction with respect to the traveling direction of the first light beam IL11 and IL12 and the first reflected light beam RL1. However, the technical idea of embodiments is not limited to this case. For example, each of the first polarizer 221_1, the compensator 221_2, and the first sub-polarizer 311 may also be rotated in a counterclockwise direction.

The first change condition (the first and second rotation angles C1 and C2) and the first blocking condition (the third rotation angle C3) may be obtained using equations (Equations 1 and 2) for a complex amplitude (E (C1, C2, C3)) and an elliptical polarization coefficient ($\psi$, $\Delta$) of the first reflected light beam RL1 and an equation (Equation 3) for the intensity of light. Here, $r_p$ is a reflection coefficient of the test region TR1 for p-polarized light and $r_s$ is a reflection coefficient of the test region TR1 for s-polarized light.

$$E(C1, C2, C3) = r_p*\cos A*[\cos(C1-C2)*\cos C2 + i*\sin C2*\sin(C2-C1)] + r_s*\sin C3*[\cos(C1-C2)*\sin C2 - i*\mathrm{con} C2*\sin(C2-C1)], \quad (1)$$

$$\tan \psi * e^{i*\Delta} = r_p/r_s, \quad (2)$$

$$I(C1, C2, C3) = |E(C1, C2, C3)|^2 \quad (3).$$

For example, the elliptical polarization coefficient ($\psi$, $\Delta$) can be obtained as in Equations 5 and 6 by using $I(0, \pi/4, 0)$, $I(0, \pi/4, \pi/4)$, and $I(\pi/4, \pi/4, \pi/2)$.

$$\tan\psi = \sqrt{I_{(0,\pi/4,0)}/I_{(\pi/4,\pi/4,\pi/2)}}, \quad (5)$$

$$\sin\Delta = \frac{I_{(0,\pi/4,0)} + I_{(\pi/4,\pi/4,\pi/2)} - 2I_{(0,\pi/4,\pi/4)}}{2\sqrt{I_{(0,\pi/4,0)}I_{(\pi/4,\pi/4,\pi/2)}}}. \quad (6)$$

Here, assuming that C3 is $\pi/4$, Equation 1 can be rearranged into Equation 7.

$$E(C1, C2, C3) = \frac{r_s}{\sqrt{2}} * \cos A * e^{-i(\frac{\pi}{4}-C1)}\left\{\frac{r_p}{r_s}*e^{i(\frac{\pi}{2}-2*C1)} + \tan C3\right\} \quad (7)$$

Assuming that E(C1, C2, C3)=0 in order to obtain the first blocking condition, the first change condition can be obtained as in Equations 8 and 9.

$$C2 = \psi, \quad (8)$$

$$C1 = \Delta/2 - \pi/4 \quad (9).$$

Although a case where $I(0, \pi/4, 0)$, $I(0, \pi/4, \pi/4)$, and $I(\pi/4, \pi/4, \pi/2)$ and Equations 1 through 6 are used to obtain the elliptical polarization coefficient ($\psi$, $\Delta$) has been described above, the technical idea of embodiments is not limited to this case. For example, the elliptical polarization coefficient ($\psi$, $\Delta$) can be obtained using other equations.

Furthermore, although a case where the first blocking condition and the first change condition are obtained using Equations 1 through 9 has been described above, the technical idea of embodiments is not limited to this case. For example, the first blocking condition and the first change condition can be obtained using equations different from Equations 1 through 9. Alternatively, the first blocking condition and the first change condition can be obtained experimentally.

The first through fourth change conditions of the first through fourth incident optical systems 201, 202, 203, and 204 may be different from each other. In addition, the first through fourth blocking conditions of the first through fourth sub-optical systems 301, 302, 303, and 304 may be different from each other.

Figure 6:
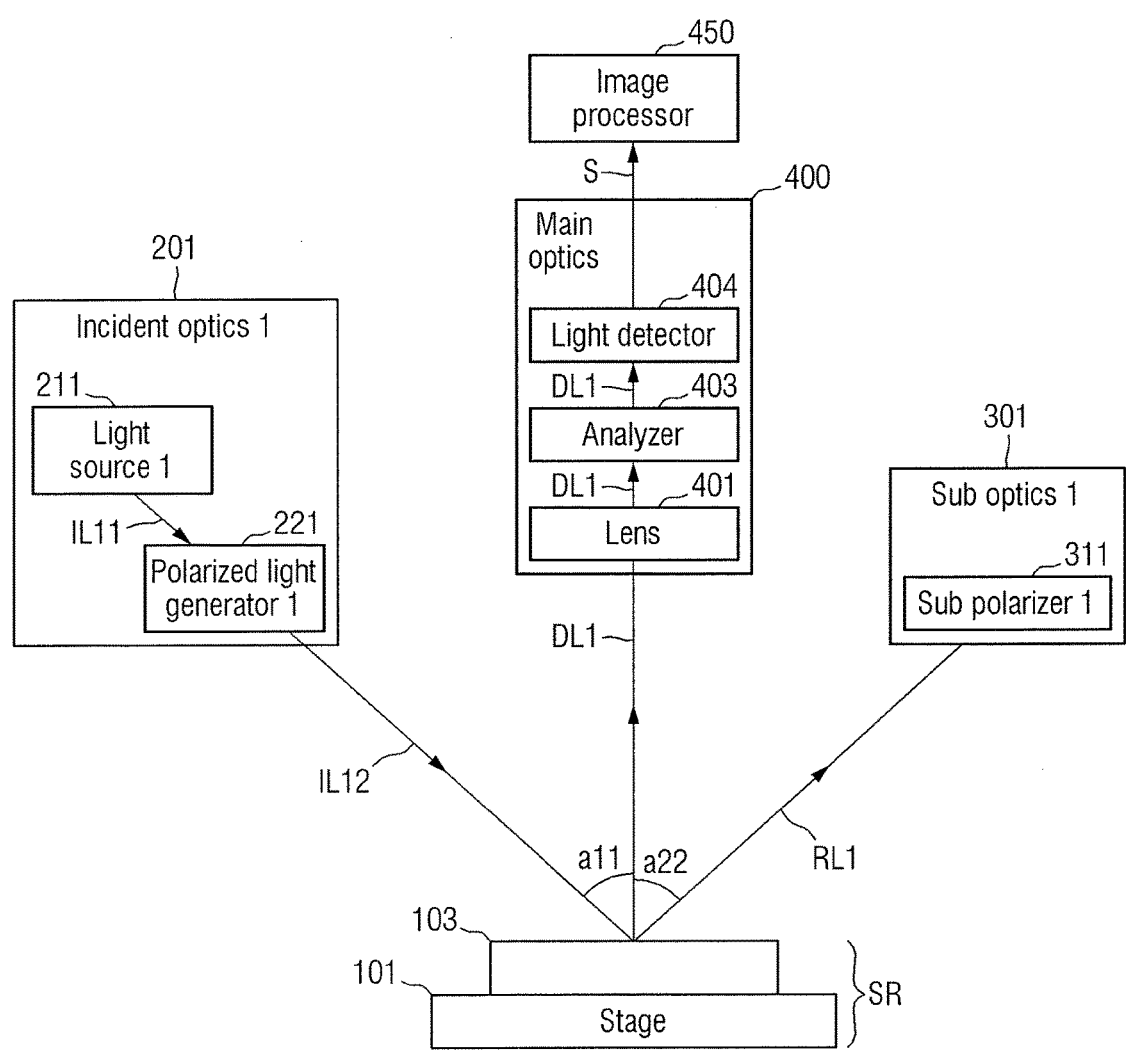
FIG. 6 illustrates a main optical system and an image processor included in the optical test system of FIG. 1.
Figure 7:
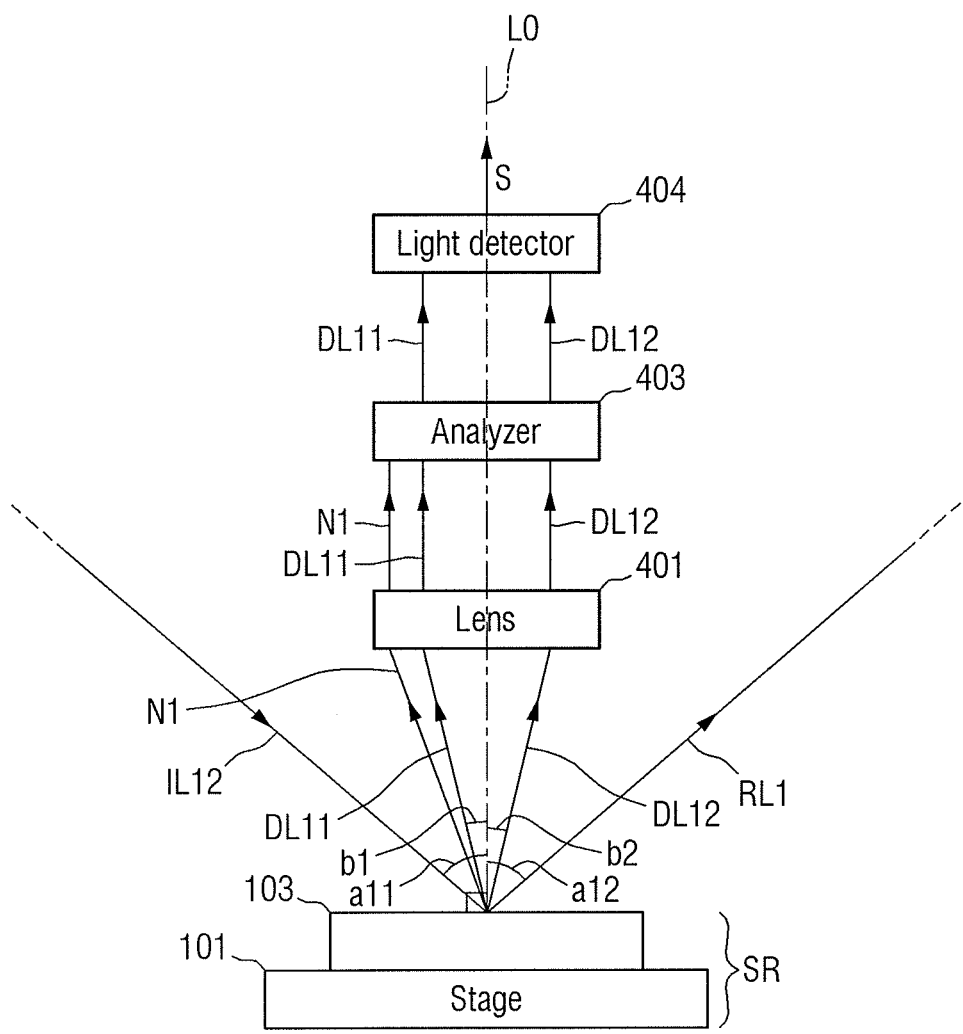
FIG. 7 illustrates the main optical system of FIG. 6.
Figure 8:
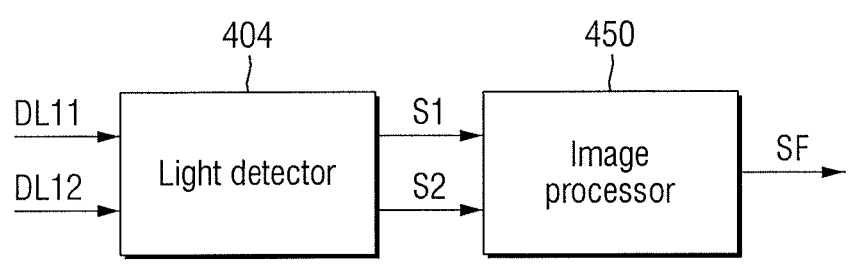
FIG. 8 illustrates the image processor of FIG. 6.

FIG. 6 illustrates the main optical system 400 and an image processor 450 included in the optical test system of FIG. 1. FIG. 7 illustrates the main optical system 400 of FIG. 6. FIG. 8 illustrates the image processor 450 of FIG. 6. For clarity of description, any redundant description will be omitted.

Referring to FIGS. 6 through 8, the main optical system 400 may receive reflected light beams DL1 reflected at reflection angles different from the first incident angle a11 among a plurality of reflected light beams (e.g., DL11, DL12, RL1, and N1) obtained after the first light beam IL12 in the second polarization state is reflected from the stage region SR. The reflected light beams DL1 reflected at the reflection angles different from the first incident angle a11 may include, e.g., a first noise N1, a third reflected light beam DL11, and a fourth reflected light beam DL12. The third reflected light beam DL11 may be a light beam reflected at the third reflection angle b1 and the fourth reflected light beam DL12 may be a light beam reflected at the fourth reflection angle b2. The third reflection angle b1 and the fourth reflection angle b2 may be closer to the virtual line L0 than any of the incident angles. In other words, the first reflected light beam RL1 reflected at the first reflection angle a12, which is the same as the first incident angle a11, may not be incident on the main optical system 400.

In some embodiments, the main optical system 400 may be positioned perpendicular to the stage region SR. The first noise N1, the third reflected light beam DL11, and the fourth reflected light beam DL12 may be incident on an analyzer 403 through a lens 401.

The analyzer 403 may be rotated at a certain angle to remove noise from incident light. For example, the analyzer 403 may pass the third reflected light beam DL11 and the fourth reflected light beam DL12 among the first noise N1, the third reflected light beam DL11, and the fourth reflected light beam DL12. The third reflected light beam DL11 and the fourth reflected light beam DL12 that pass through the analyzer 403 may be incident on a light detector 404. The rotation angle of the analyzer 403 may be calculated using the third rotation angle C3, but the technical idea of embodiments is not limited to this case. For example, the rotation angle of the analyzer 403 may be experimentally determined to remove noise.

The light detector 404 may generate first image data S1 and second image data S2 for the third reflected light beam DL11 and the fourth reflected light beam DL12 using the third reflected light beam DL11 and the fourth reflected light beam DL12, respectively. The main optical system 400 may provide generated image data S to the image processor 450. The image data S may include the first image data S1 and the second image data S2.

The image processor 450 may process the image data S to generate final image data SF. The final image data SF may include information about a defect existing in the object 103.

In the drawings, the image processor 450 is disposed separately from the main optical system 400. However, embodiments are not limited to this case. For example, the image processor 450 may be included in the main optical system 400.

An optical test system according to embodiments will now be described with reference to FIGS. 9 through 11. For clarity, any redundant description will be omitted.

Figure 9:
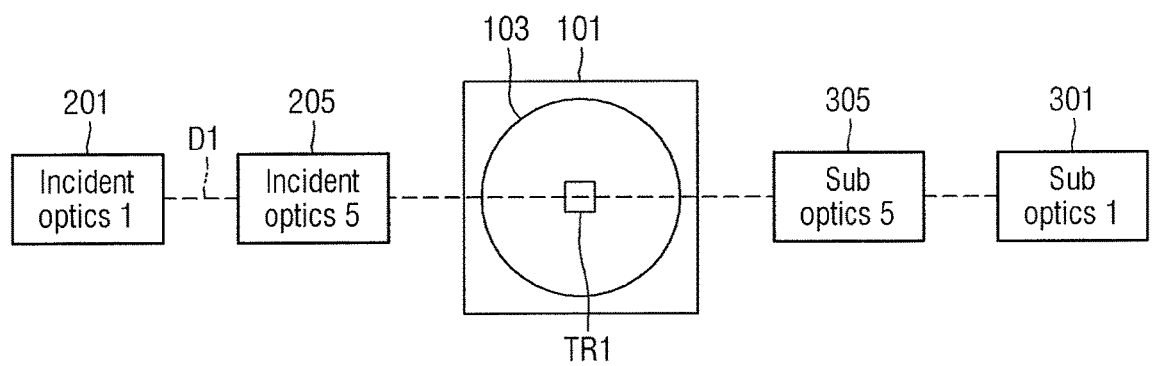
FIG. 9 illustrates a conceptual plan view of an optical test system according to embodiments.

FIG. 9 is a conceptual plan view of an optical test system according to embodiments. In FIG. 9, a main optical system 400 and an image processor 450 are omitted for clarity. FIG. 10 shows a side view of the optical test system of FIG. 9 to describe the optical test system according to the embodiments. FIG. 11 illustrates the main optical system 400 of FIG. 10.

Figure 10:
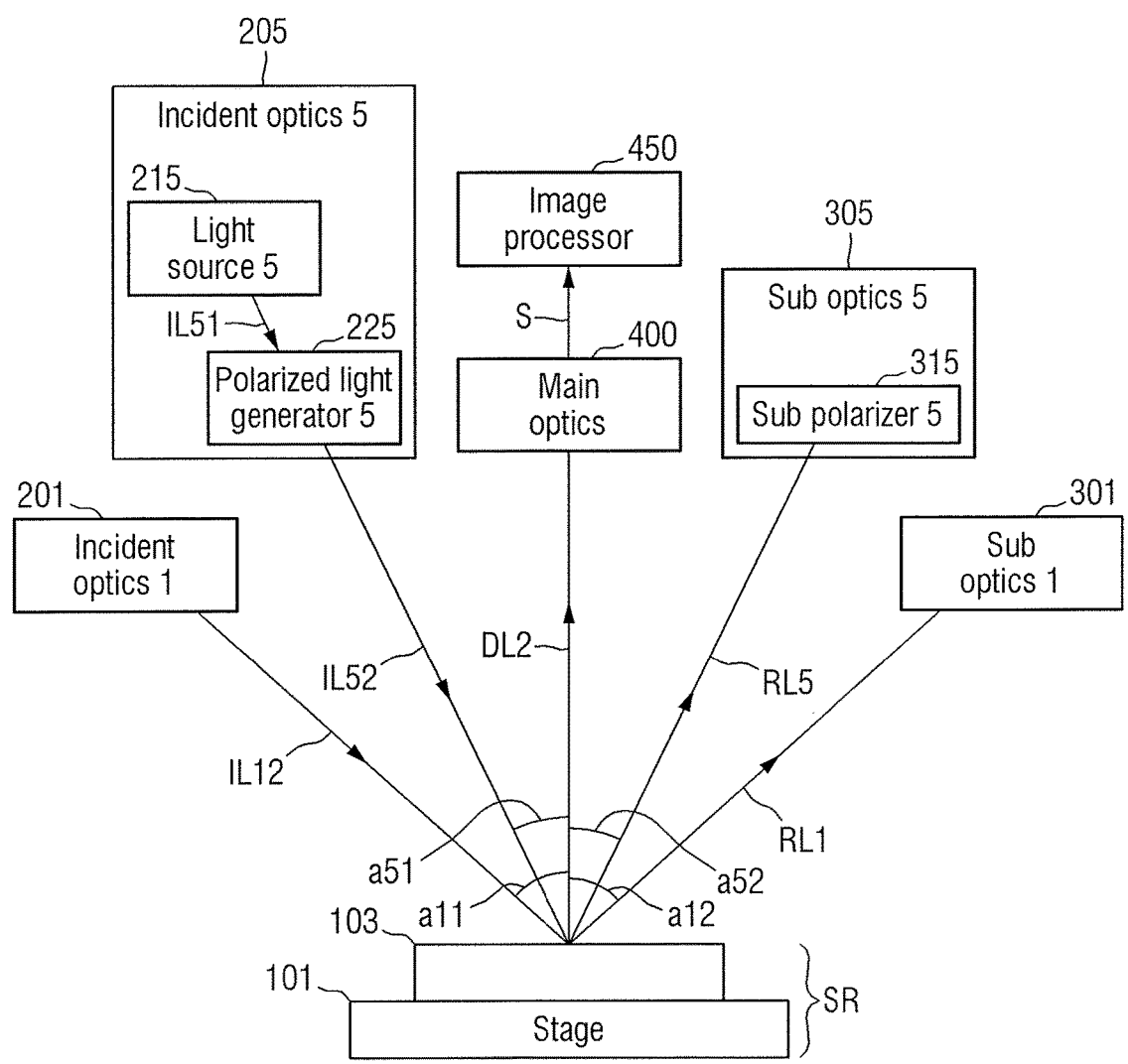
FIG. 10 illustrates a side view of the optical test system of FIG. 9 to describe the optical test system according to the embodiments.
Figure 11:
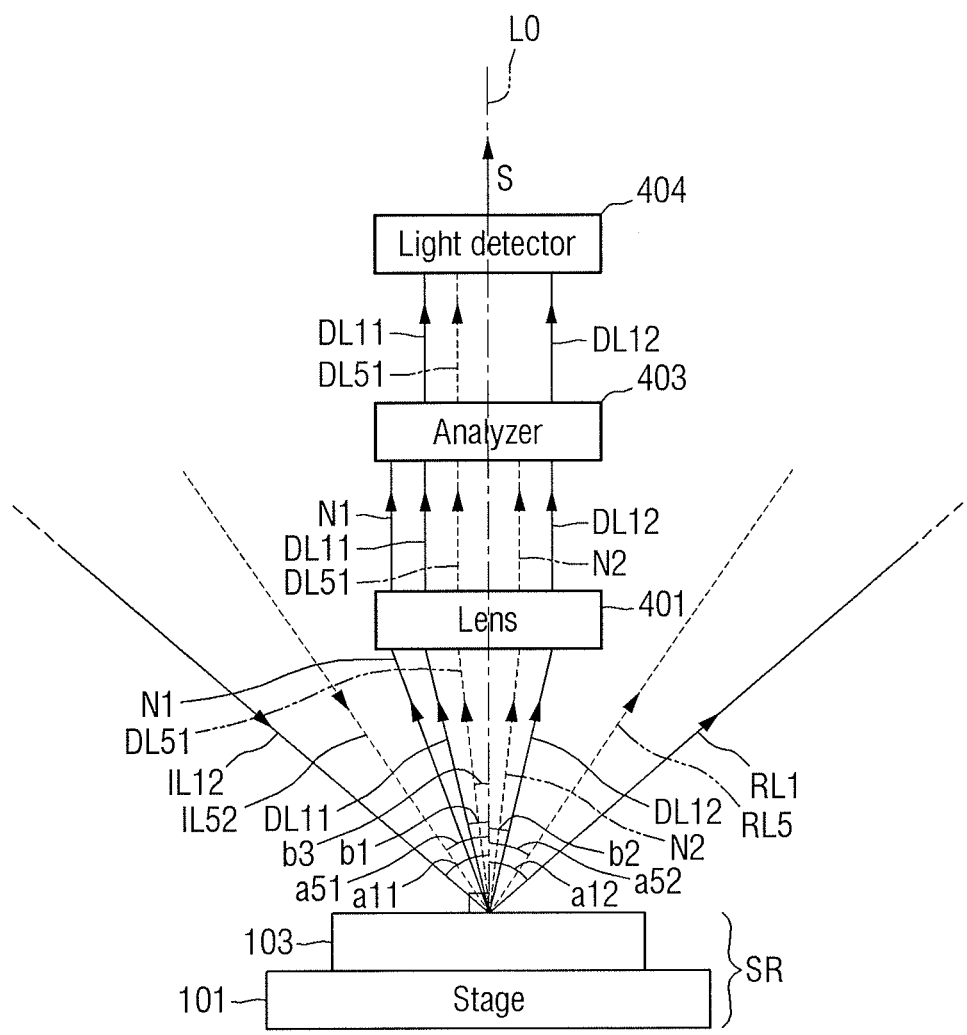
FIG. 11 illustrates a main optical system of FIG. 10.

Referring to FIGS. 9 through 11, a fifth incident optical system 205 and a fifth sub-optical system 305 corresponding to the fifth incident optical system 205 may be separated from a first incident optical system 201 and a first sub-optical system 301 in a first direction D1. The fifth incident optical system 205 and the fifth sub-optical system 305 corresponding to the fifth incident optical system 205 may be paired with each other.

The fifth incident optical system 205 may include a fifth light source 215 and a fifth polarized light generator 225. The fifth light source 215 may provide a fifth light beam IL51 in a fifth polarization state to the fifth polarized light generator 225.

The fifth polarized light generator 225 may change the fifth polarization state of the fifth light beam IL51 to a sixth polarization state. A fifth light beam IL52 in the sixth polarization state may be incident on a stage region SR at a fifth incident angle a51. The sixth polarization state may be, e.g., an elliptical polarization state. That is, the fifth polarized light generator 225 may change the polarization state of incident light to, e.g., the elliptical polarization state.

The fifth light source 215 and the fifth polarized light generator 225 may provide the fifth light beam IL52 in the sixth polarization state to a test region TR1 at the fifth incident angle a51. Here, the fifth incident angle a51 may be a value relative to the virtual line L0 perpendicular to the upper surface of the stage 101. In other words, the fifth incident optical system 205 may provide the fifth light beam IL52 in the sixth polarization state to the stage region SR in the first direction D1 at the fifth incident angle a51.

The fifth incident angle a51 may not be a right angle. In other words, light beams incident on the stage region SR by the fifth incident optical system 205 may not be perpendicular to the upper surface of the stage 101. In some embodiments, the fifth incident angle a51 may have a different value from a first incident angle a11.

A plurality of reflected light beams (e.g., DL11, DL51, DL12, RL1, RL5, N1, and N2) may include reflected light beams DL51 and N2 obtained after the fifth light beam IL52 in the sixth polarization state is reflected from the stage region SR.

The fifth sub-optical system 305 may receive a fifth reflected light beam RL5 obtained after the fifth light beam IL52 in the sixth polarization state is specularly reflected from the stage region SR, among the reflected light beams (e.g., DL11, DL51, DL12, RL1, RL5, N1, and N2). The fifth reflected light beam RL5 may be a light beam reflected from the stage region SR at a fifth reflection angle a52. The fifth reflection angle a52 may be the same as the fifth incident angle a51. The fifth reflected light beam RL5 may be, for example, a linearly polarized light beam.

Light beams (e.g., DL11, DL51, DL12, N1, and N2) other than the fifth specularly reflected light beam RL5 from the reflected light beams (e.g., DL11, DL51, DL12, RL1, RL5, N1 and N2) may be received by the main optical system 400. Each of the reflected light beams (e.g., DL11, DL51, DL12, N1, and N2) other than the fifth specularly reflected light beam RL5 from the reflected light beams (e.g., DL11, DL51, DL12, RL1, RL5, N1, and N2) may be a light beam reflected from the stage region SR at a reflection angle different from the fifth incident angle a51. In other words, a sixth reflection angle b3 may not be the same as any of the first incident angle a11 and the fifth incident angle a51.

The fifth sub-optical system 305 may include a fifth sub-polarizer 315. The fifth sub-polarizer 315 may be substantially similar to a first sub-polarizer 311. For example, a fifth blocking condition may be different from the first blocking condition. However, the function of the fifth sub-polarizer 315 may be substantially the same as that of the first sub-polarizer 311.

The main optical system 400 may receive reflected light beams DL2 reflected at reflection angles different from the first and second incident angles a11 and a51 among a plurality of reflected light beams (e.g., DL11, DL51, DL12, RL1, RL5, N1 and N2) obtained after a first light beam IL12 in a second polarization state and the fifth light beam IL52 in the sixth polarization state are reflected from the stage SR.

The reflected light beams DL2 reflected at the reflection angles different from the first and fifth incident angles a11 and a51 may include, for example, the first noise N1, a second noise N2, the third reflected light beam DL11, the fourth reflected light beam DL12, and a sixth reflected light beam DL51. The third reflected light beam DL11 may be a light beam reflected at the sixth reflection angle b3.

The first noise N1, the second noise N2, the third reflected light beam DL11, the fourth reflected light beam DL12, and the sixth reflected light beam DL51 may pass through the lens 401 to be incident on the analyzer 403. The analyzer 403 may be rotated at a certain angle to remove noise from incident light.

For example, the analyzer 403 may transmit the third reflected light beam DL11, the fourth reflected light beam DL12, and the sixth reflected light beam DL51 among the first noise N1, the second noise N2, the third reflected light beam DL11, the fourth reflected light beam DL12 and the sixth reflected light beam DL51, while blocking the first noise N1 and the second noise N2 The third reflected light beam DL11 the fourth reflected light beam DL12, and the sixth reflected light beam DL51 that pass through the analyzer 403 may be incident on a light detector 404.

The light detector 404 may generate third image data for the sixth reflected light beam DL51. Image data S may further include the third image data.

An optical test system according to embodiments will now be described with reference to FIG. 12. For clarity, any redundant description will be omitted.

Figure 12:
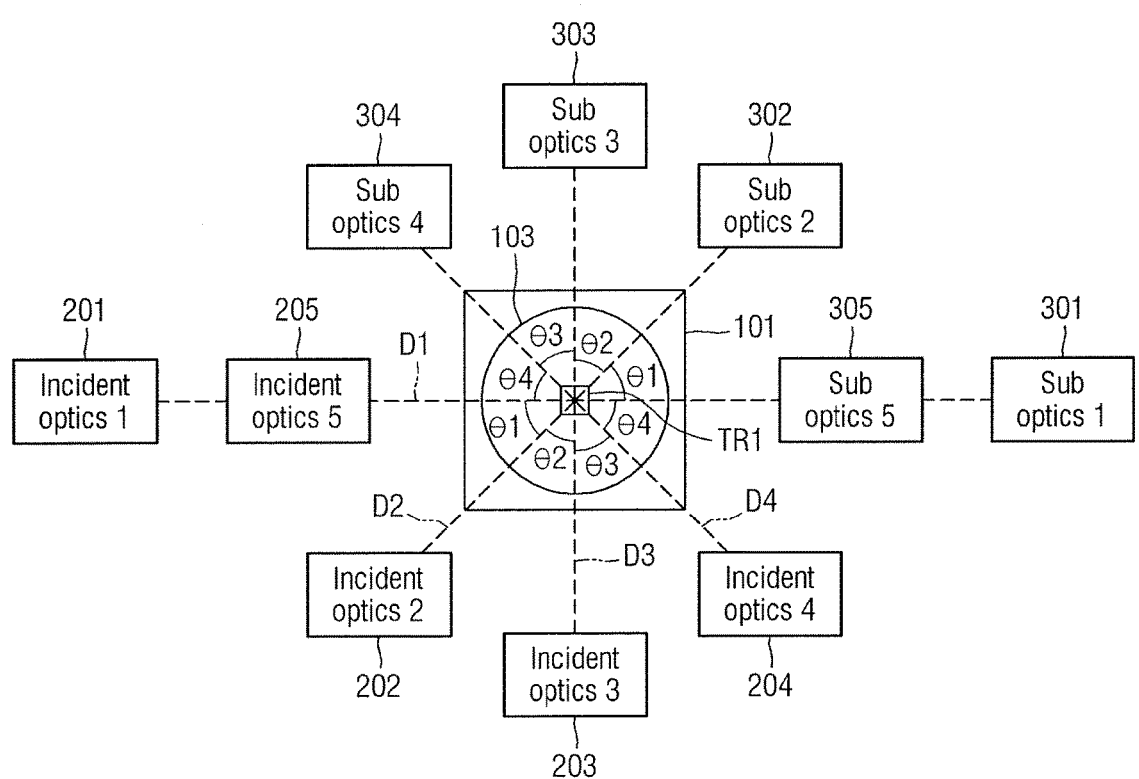
FIG. 12 illustrates a conceptual plan view of an optical test system according to embodiments.

FIG. 12 is a conceptual plan view of an optical test system according to embodiments. In FIG. 12, a main optical system 400 (see FIG. 6) and an image processor 450 (see FIG. 6) are omitted for clarity of illustration.

Referring to FIG. 12, first through fourth incident optical systems 201 through 204 may be disposed in different directions from a stage region SR (specifically, a test region TR1). The fifth incident optical system 205 may be disposed in a first direction D1. First through fifth sub-optical test systems 301 through 305 may be placed to correspond to the first through fifth incident optical systems 201 through 205, respectively.

Figure 13:
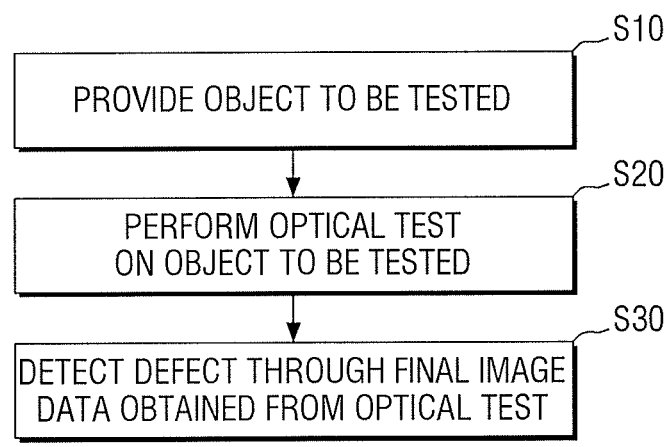
FIGS. 13 and 14 respectively illustrate flowcharts of an optical test method and a method of manufacturing a semiconductor device by using the optical test method according to embodiments.
Figure 14:
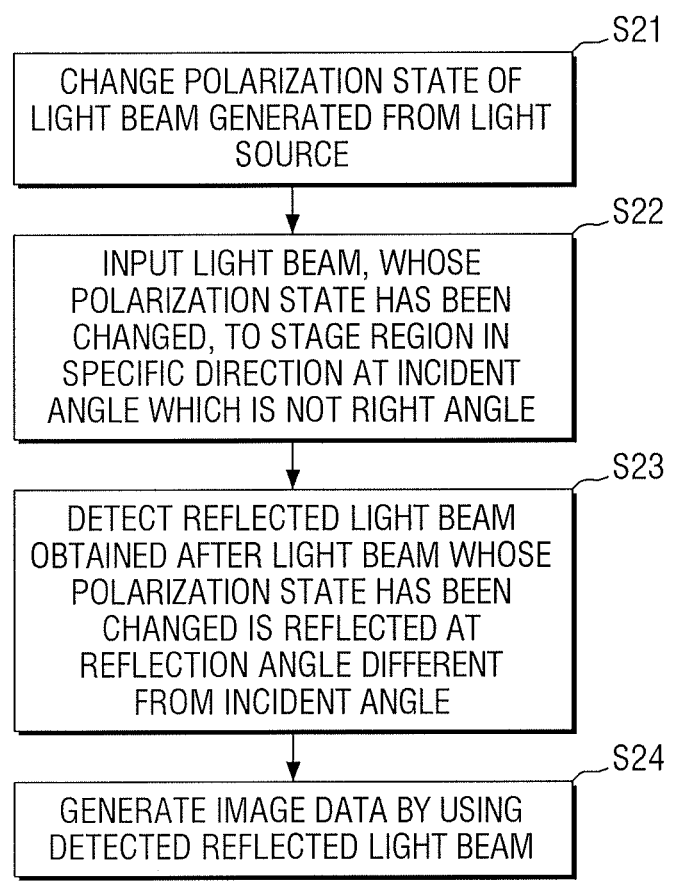

An optical test method and a method of manufacturing a semiconductor device using the optical test method according to embodiments will now be described with reference to FIGS. 13 and 14. FIGS. 13 and 14 are flowcharts respectively illustrating an optical test method and a method of manufacturing a semiconductor device by using the optical test method according to embodiments.

Referring to FIG. 13, an object to be tested may be provided in operation S10. The object 103 to be tested may be, e.g., a semiconductor wafer or a patterned semiconductor device.

In operation S20, an optical test may be performed on the object to be tested. The optical test on the object to be tested, e.g., on a semiconductor wafer or a patterned semiconductor device, may be performed, e.g., during the process of manufacturing a semiconductor device.

Referring to FIG. 14, operation S20 of FIG. 13 may include operations S21 through S24.

In operation S21 of FIG. 14, the polarization state of a light beam generated from a light source may be changed.

In operation S22 of FIG. 14, the light beam whose polarization state has changed may be incident on a stage region in a specific direction at an incident angle. The incident angle may not be, for example, a right angle. For example, a first light beam IL12 (see FIG. 3) which has been changed from a first polarization state to a second polarization state may be incident on the stage region in a first direction D1 (see FIG. 1) at a first incident angle a11 (see FIG. 3) which is not a right angle.

In operation S23 of FIG. 14, a reflected light beam obtained after the light beam whose polarization state has been changed is reflected from the stage region at a reflection angle different from the incident angle may be detected. For example, a third reflected light beam DL11 (see FIG. 7) obtained after the first light beam IL12 (see FIG. 7) in the second polarization state is reflected from the stage region in the first direction D1 at a third reflection angle b1 different from the first incident angle a11 (see FIG. 7) may be detected. That is, the size of the first incident angle a11 may be different from the size of the third reflection angle b1.

In operation S24 of FIG. 14, image data may be generated using the detected reflected light beam. For example, image data for the third reflected light beam DL11 (see FIG. 7) may be generated using the third reflected light beam DL11 (see FIG. 7).

Operations S21 through S24 of FIG. 14 may be repeatedly performed in second through fourth directions D2 through D4 (see FIG. 1).

Referring to FIG. 13, in operation S30, a defect existing in the object to be tested may be detected through final image data obtained from the optical test. Since operations S21 through S24 of FIG. 14 are repeatedly performed in different directions (D1 through D4 in FIG. 1), image data detected in each direction may be processed to generate the final image data. Through the final image data, a defect existing in the object to be tested may be detected.

In an optical test system, an optical test method, and a method of manufacturing a semiconductor device by using the optical test system and the optical test method according to embodiments, image data is generated using only a reflected light beam including information about a defect existing in an object to be tested among a plurality of reflected light beams. Therefore, a defect can be detected effectively. In addition, an analyzer of a main optical system is rotated at a certain angle to detect the reflected light beam including the information about a defect existing in the object to be tested among the reflected light beams. Therefore, noise can be removed from the reflected light beams.

In the optical test system, the optical test method, and the method of manufacturing a semiconductor device by using the optical test system and the optical test method according to the embodiments, since light beams are incident in different directions, a defect in a test region can be rapidly detected. In addition, since light beams are incident in different directions and image data is generated by using only a reflected light beam including information about a defect existing in an object to be tested among a plurality of reflected light beams, even a nano-sized defect can be detected. Further, in the optical test system, the optical test method, and the method of manufacturing a semiconductor device by using the optical test system and the optical test method according to the embodiments, light beams incident on an object to be tested in different directions are used, and image data is generated by performing image processing on a plurality of reflected light beams including information about defects existing in an object to be tested. Therefore, the accuracy of defect detection can be improved. For example, when light beams incident on an object to be tested in different directions are used and when image data is generated by performing image processing on a plurality of reflected light beams including information about defects existing in the object to be tested, the roughness of the surface of the object to be tested can be distinguished from defects existing in the object to be tested. Thus, the accuracy of defect detection can be improved.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An optical test system, comprising:
a stage region to accommodate an object to be tested;
a first incident optical system to change a first polarization state of a first light beam to a second polarization state and to direct the first light beam in the second polarization state onto the stage region in a first direction at a first incident angle which is not a right angle;
a second incident optical system to change a third polarization state of a second light beam to a fourth polarization state and to direct the second light beam in the fourth polarization state onto the stage region in a second direction, which is different from the first direction by a first angle, at a second incident angle which is not a right angle; and
a main optical system to detect a first reflected light beam, reflected at a first reflection angle different from the first incident angle and the second incident angle, among a plurality of reflected light beams obtained after the first light beam in the second polarization state is reflected from the stage region.

2. The optical test system as claimed as claim 1, further comprising a detector to generate first image data using the first reflected light beam.

3. The optical test system as claimed as claim 1, wherein the reflected light beams include reflected light beams obtained after the second light beam in the fourth polarization state is incident on the stage region and then reflected from the stage region, and the main optical system is to detect a second reflected light beam, reflected at a second reflection angle different from the first incident angle and the second incident angle, among the reflected light beams.

4. The optical test system as claimed as claim 3, wherein the main optical system includes an analyzer to transmit the first reflected light beam and the second reflected light beam, wherein the analyzer is rotated at a certain angle to transmit the first reflected light beam and the second reflected light beam among the reflected light beams.

5. The optical test system as claimed as claim 1, further comprising a third incident optical system to change a fifth polarization state of a third light beam to a sixth polarization state and to direct the third light beam in the sixth polarization state to the stage region in the first direction at a third incident angle which is not a right angle,
wherein the third incident angle is different from the first incident angle,
the reflected light beams include reflected light beams obtained after the third light beam in the sixth polarization state is incident on the stage region and then reflected from the stage region, and
the main optical system is to detect a third reflected light beam reflected at a third reflection angle different from the third incident angle among the reflected light beams.

6. The optical test system as claimed as claim 5, further comprising:
a detector to generate first image data from the first reflected light beam and to generate third image data from the third reflected light beam; and
an image data processor to process the first image data and the third image data and to generate final image data.

7. The optical test system as claimed as claim 1, further comprising a third incident optical system to change a fifth polarization state of a third light beam to a sixth polarization state and to direct the third light beam in the sixth polarization state onto the stage region in a third direction, which is different from the second direction by a second angle, at a third incident angle which is not a right angle,
wherein the reflected light beams include reflected light beams obtained after the third light beam in the sixth polarization state is incident on the stage region and then reflected from the stage region, and
the main optical system to detect a third reflected light beam, reflected at a third reflection angle different from the first to third incident angles, among the reflected light beams.

8. A method of manufacturing a semiconductor device, the method comprising:
providing an object to be tested; and
performing an optical test on the object to be tested,
wherein performing the optical test on the object to be tested includes:
changing a first polarization state of a first light beam to a second polarization state;
providing the first light beam in the second polarization state to a test region of the object to be tested in a first direction at a first incident angle which is not a right angle;
detecting a first reflected light beam, reflected at a first reflection angle different from the first incident angle, among a plurality of reflected light beams obtained after the first light beam in the second polarization state is incident on the test region and then reflected from the test region;
obtaining first image data from the first reflected light beam;
changing a third polarization state of a second light beam to a fourth polarization state;
providing the second light beam in the fourth polarization state to the test region in a second direction, which is different from the first direction by a first angle, at a second incident angle which is not a right angle;
detecting a second reflected light beam, reflected at a second reflection angle different from the first and second incident angles, among the reflected light beams which include reflected light beams obtained after the second light beam in the fourth polarization state is incident on the test region and then reflected from the test region;
obtaining second image data from the second reflected light beam; and
generating final image data by processing the first image data and the second image data.

9. The method as claimed as claim 8, wherein performing the optical test on the object to be tested further includes:
changing a fifth polarization state of a third light beam to a sixth polarization state;
providing the third light beam in the sixth polarization state to the test region in the first direction at a third incident angle which is not a right angle; and
detecting a third reflected light beam, reflected at a third reflection angle different from the first to third incident angles, among the reflected light beams which include reflected light beams obtained after the third light beam in the sixth polarization state is incident on the test region and then reflected from the test region,
wherein the third incident angle is different from the first incident angle.

10. The method as claimed as claim 9, further comprising obtaining third image data by using the third reflected light beam, wherein the generating of the final image data further includes processing the third image data.

11. The method as claimed as claim 8, wherein performing the optical test on the object to be tested further includes:
changing a fifth polarization state of a third light beam to a sixth polarization state;
directing the third light beam in the sixth polarization state onto the test region in a third direction, which is different from the second direction by a second angle, at a third incident angle which is not a right angle; and
detecting a third reflected light beam, reflected at a third reflection angle different from the third incident angle, among the reflected light beams which include reflected light beams obtained after the third light beam in the sixth polarization state is incident on the test region and then reflected from the test region.

12. The method as claimed as claim 11, further comprising obtaining third image data by using the third reflected light beam, wherein the generating of the final image data further includes processing the third image data.

13. The method as claimed as claim 8, wherein performing the optical test on the object to be tested further includes:
setting a change condition for changing the first polarization state of the first light beam to the second polarization state; and
setting a blocking condition for receiving a third reflected light beam obtained after the first light beam in the second polarization state is specularly reflected from the test region and passing one two-hundred-thousandth or less of the third reflected light beam.

14. An optical test method, comprising:
changing a first polarization state of a first light beam to a second polarization state;

providing the first light beam in the second polarization state onto a stage region in a first direction at a first incident angle which is not a right angle;

detecting a first reflected light beam reflected at a first reflection angle different from the first incident angle among a plurality of reflected light beams obtained after the first light beam in the second polarization state is reflected from the stage region;

changing a third polarization state of a second light beam to a fourth polarization state;

providing the second light beam in the fourth polarization state onto the stage region in a second direction, which is different from the first direction by a first angle, at a second incident angle which is not a right angle; and detecting a second reflected light beam, reflected at a second reflection angle different from the second incident angle, among the reflected light beams which include reflected light beams obtained after the second light beam in the fourth polarization state is incident on the stage region and then reflected from the stage region.

15. The method as claimed as claim 14, further comprising:
   obtaining first image data using the first reflected light beam; and
   obtaining second image data using the second reflected light beam.

16. The method as claimed as claim 15, further comprising generating final image data by processing the first image data and the second image data.

17. The method as claimed as claim 14, further comprising:
   changing a fifth polarization state of a third light beam to a sixth polarization state;
   providing the third light beam in the sixth polarization state onto the stage region in the first direction at a third incident angle which is not a right angle; and
   detecting a third reflected light beam, reflected at a third reflection angle different from the third incident angle, among the reflected light beams which include reflected light beams obtained after the third light beam in the sixth polarization state is incident on the stage region and then reflected from the stage region,
   wherein the third incident angle is different from the first incident angle.

18. The method as claimed as claim 17, further comprising:
   obtaining first image data by using the first reflected light beam;
   obtaining second image data by using the second reflected light beam;
   obtaining third image data by using the third reflected light beam; and
   processing the first image data, the second image data and the third image data.

19. The method as claimed as claim 14, further comprising:
   changing a fifth polarization state of a third light beam to a sixth polarization state;
   directing the third light beam in the sixth polarization state onto the stage region in a third direction, which is different from the second direction by a second angle, at a third incident angle which is not a right angle; and
   detecting a third reflected light beam reflected at a third reflection angle different from the third incident angle among the reflected light beams which include reflected light beams obtained after the third light beam in the sixth polarization state is incident on the stage region and then reflected from the stage region.

20. The method as claimed as claim 14, further comprising:
   setting a change condition for changing the first polarization state of the first light beam to the second polarization state; and
   setting a blocking condition to pass one two-hundred-thousandth or less of a third reflected light beam reflected at the first incident angle from the stage region.

* * * * *